(12) United States Patent
Kirby et al.

(10) Patent No.: US 12,721,941 B2
(45) Date of Patent: Sep. 1, 2026

(54) NOISE-REDUCING SURGICAL ASPIRATOR

(71) Applicant: THE CURATORS OF THE UNIVERSITY OF MISSOURI, Columbia, MO (US)

(72) Inventors: Benjamin Jay Kirby, Columbia, MO (US); Ethan John Whitaker, Columbia, MO (US); Addison Diann Logsdon, Columbia, MO (US); Isabel Sidney Ives, Columbia, MO (US); Britton William Stamps, Columbia, MO (US); Jackson Stephen Eisenhauer, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 330 days.

(21) Appl. No.: 18/617,844

(22) Filed: Mar. 27, 2024

(65) Prior Publication Data

US 2024/0350718 A1 Oct. 24, 2024

Related U.S. Application Data

(60) Provisional application No. 63/496,812, filed on Apr. 18, 2023.

(51) Int. Cl.
*A61M 1/00* (2006.01)

(52) U.S. Cl.
CPC ................ *A61M 1/87* (2021.05); *A61M 1/76* (2021.05); *A61M 2205/42* (2013.01)

(58) Field of Classification Search
CPC ...... A61M 1/87; A61M 1/76; A61M 2205/42; A61M 1/74; A61M 2205/3331; A61M 16/0666; A61M 1/77; A61M 1/96; A61M 1/84; A61M 1/80; A61M 1/774; A61B 2217/005
See application file for complete search history.

(56) References Cited

U.S. PATENT DOCUMENTS

| | | | | |
|---|---|---|---|---|
| 4,685,534 | A * | 8/1987 | Burstein | F01N 13/1894 181/251 |
| 10,737,001 | B2 * | 8/2020 | Yarger | A61M 1/84 |
| 2011/0028939 | A1 * | 2/2011 | Yarger | A61M 1/84 604/523 |
| 2023/0041941 | A1 * | 2/2023 | Farokhi | F01N 1/14 |

* cited by examiner

*Primary Examiner* — Adam Marcetich
*Assistant Examiner* — Brandon W. Levy
(74) *Attorney, Agent, or Firm* — McKee, Voorhees & Sease, PLC

(57) ABSTRACT

A noise-reducing surgical aspirator that includes a tube, a handle, having a first end portion, a second end portion, and a first internal fluid conduit, where the first end portion of the handle is attached to the tube in fluid communication, and a surgical aspirator tip having a second internal fluid conduit that is in fluid communication with the first internal fluid conduit of the handle and having a first end portion attached to the second end portion of the handle and having a second end portion having an opening, wherein the second internal fluid conduit of the surgical aspirator tip includes a first inner recessed radius and a second radius with a first fillet located between the first inner recessed radius and the second radius and also includes a third outer radius of the opening and a second fillet located between the second radius and the third outer radius.

7 Claims, 6 Drawing Sheets

NOISE-REDUCING SURGICAL ASPIRATOR

CROSS REFERENCE TO RELATED APPLICATIONS

This application claims priority under 35 U.S.C. § 119 to provisional patent application U.S. Ser. No. 63/496,812, filed Apr. 18, 2023. The provisional patent application is herein incorporated by reference in its entirety, including, without limitation, the specification, claims, and abstract, as well as any figures, tables, appendices, or drawings thereof.

FIELD OF THE INVENTION

The present invention generally relates to a novel surgical aspirator to lower noise distraction for those in the operating room.

BACKGROUND OF THE INVENTION

A surgical aspirator can be used for a variety of things and has multiple components, including but not limited to, a line-powered vacuum pump, a vacuum regulator, a gauge, a collection canister, and an optional bacterial filter. Tubing connects these components, completing an open-ended system that continuously draws tissue, debris, and fluid from the surgical field to the collection canister. The tip of the surgical aspirator can also be used in manipulating tissue during surgery; hence, there must be some sturdiness on the more extended portion of the surgical aspirator tip. Unfortunately, these surgical aspirator devices are known to create noises exceeding 120 dB, which can be distracting for the surgeon, nurses, and anyone else who may be in the operating room. This noise can worsen communication skills and lower performance, all of which can be disastrous in an operating setting.

Although the suction device is helpful and extremely necessary, the device is also a source of distraction for many personnel in the operating room. The distraction originates from the harsh noise levels that a surgical aspirator can generate, especially when using high suction pressure. The noise can lead to communication difficulties and has been proven to cause fatigue for surgeons and other personnel.

Although laminar flow is preferred to reduce noise, as shown in FIG. 1 by numeral 10, the turbulent flow at the tip of the surgical aspirator suction device can produce sound levels exceeding 120 dB, as shown by numeral 12 in FIG. 2, which is the equivalent to a concert, disco, or shotgun blast. These levels of noise only add to the already noisy operating room environment. Studies have shown that a consistently loud environment can cause a decline in effective communication, cognitive skills, and performance. In operating rooms, this can result in potentially fatal errors.

Additionally, OSHA does not recommend continuous exposure to noises above 85 dB for more than eight hours, as this can result in permanent auditory impairment. The standards most important for designing a silent surgical aspirator are ISO 10079, ISO 10993, and ISO 3744. ISO 10079 is a set of standards ranging over multiple years and sections encompassing most aspects of medical suction devices. These standards include physical characteristics and functions. Safety, performance, and interface standards are also identified. ISO 10993 is a set of standards regarding biocompatibility with medical devices. This standard evaluates if a material is appropriate for a specific medical application, ensuring that device materials do not harm patients. Finally, ISO 3744 is a set of standards for determining sound power and sound energy levels in devices.

Thus, there exists a need in the art for a surgical aspirator that reduces the noise of turbulent flow, that is also low cost, sterilizable, user-friendly, and serves the surgical aspirator's purpose of suctioning.

SUMMARY OF THE INVENTION

The following objects, features, advantages, aspects, and/or embodiments, are not exhaustive and do not limit the overall disclosure. No single embodiment needs to provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

An aspect of the invention includes a noise-reducing surgical aspirator that includes a tube, a handle, having a first end portion, a second end portion, and a first internal fluid conduit, where the first end portion of the handle is attached to the tube in fluid communication and a surgical aspirator tip having a second internal fluid conduit that is in fluid communication with the first internal fluid conduit of the handle and having a first end portion attached to the second end portion of the handle and having a second end portion that includes an opening, wherein the second internal fluid conduit of the surgical aspirator tip includes a first inner recessed radius and a second radius with a first fillet located between the first inner recessed radius and the second radius and includes a third outer radius of the opening and a second fillet located between the second radius and the third outer radius.

Another aspect of the invention includes a first fillet that has a length in a range between a length of the noise-reducing surgical aspirator and is greater than one millimeter.

Still another aspect of the invention is that the second fillet has a length that is greater than four millimeters.

Yet still another aspect of the invention is that the first inner recessed radius has a radius of that of the tube.

Still yet another aspect of the invention is the second radius has a radius that is a range of two times the first inner recessed radius to 1.2 times the first inner recessed radius.

Still another aspect of the present invention is a second radius, a length that is in a range from zero millimeters to two millimeters.

Another aspect of the invention is that the third outer radius has a radius in a range of three times the first inner recessed radius to 1.2 times the second radius.

Still yet another aspect of the invention is a handle that includes a thumb indentation.

In yet another aspect of the invention, is a handle that is hexagonally shaped.

Still yet another aspect of the invention is a hexagonally shaped handle that includes a thumb indentation.

In yet another aspect of the invention is a handle that is triangularly shaped.

Another aspect of the present invention is a triangularly shaped handle that includes a thumb indentation.

Yet another aspect of the present invention is the handle, which includes a circular protrusion for attachment to the tube.

In another aspect of the invention, a noise-reducing surgical aspirator includes a tube, a handle, having a first end portion, a second end portion, and a first internal fluid conduit, a handle, having a first end portion, a second end portion, and a first internal fluid conduit, where the first end portion of the handle is attached to the tube in fluid communication, and a surgical aspirator tip having a second internal fluid conduit that is in fluid communication with the first internal fluid conduit of the handle and having a first end portion attached to the second end portion of the handle and having a second end portion that includes an opening, wherein the second internal fluid conduit of the surgical aspirator tip includes a first inner recessed radius and a second radius with a first fillet located between the first inner recessed radius and the second radius and includes a third outer radius of the opening and a second fillet located between the second radius and the third outer radius, wherein the first fillet has a length that is in a range between a length of the noise-reducing surgical aspirator and is greater than one millimeter and the second fillet has a length that is greater than four millimeters, and the first inner recessed radius has a radius that is comparable to a radius of the tube and the second radius has a radius that is a range of two times the first inner recessed radius to 1.2 times the first inner recessed radius, the second radius extends a length that is in a range from zero millimeters to two millimeters, and the third outer radius has a radius that is a range of three times the first inner recessed radius to 1.2 times the second radius.

In still yet another aspect of the invention, a method for utilizing a noise-reducing surgical aspirator includes attaching a tube to a handle, having a first end portion, a second end portion, and a first internal fluid conduit, where the first end portion of the handle is in fluid communication with the tube, and attaching a surgical aspirator tip, having a second internal fluid conduit that is in fluid communication with the first internal fluid conduit of the handle and having a first end portion attached to the second end portion of the handle, and having a second end portion that includes an opening, wherein the second internal fluid conduit of the surgical aspirator tip includes a first inner recessed radius and a second radius with a first fillet located between the first inner recessed radius and the second radius and includes a third outer radius of the opening and a second fillet located between the second radius and the third outer radius.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

An artisan of ordinary skill in the art need not view, within the isolated figure(s), the near infinite number of distinct permutations of features described in the following detailed description to facilitate an understanding of the present invention.

DETAILED DESCRIPTION OF THE INVENTION

The present disclosure is not to be limited to that described herein. Mechanical, electrical, chemical, procedural, and/or other changes can be made without departing from the spirit and scope of the present invention. No features shown or described are essential to permit the basic operation of the present invention unless otherwise indicated.

Figure 1:
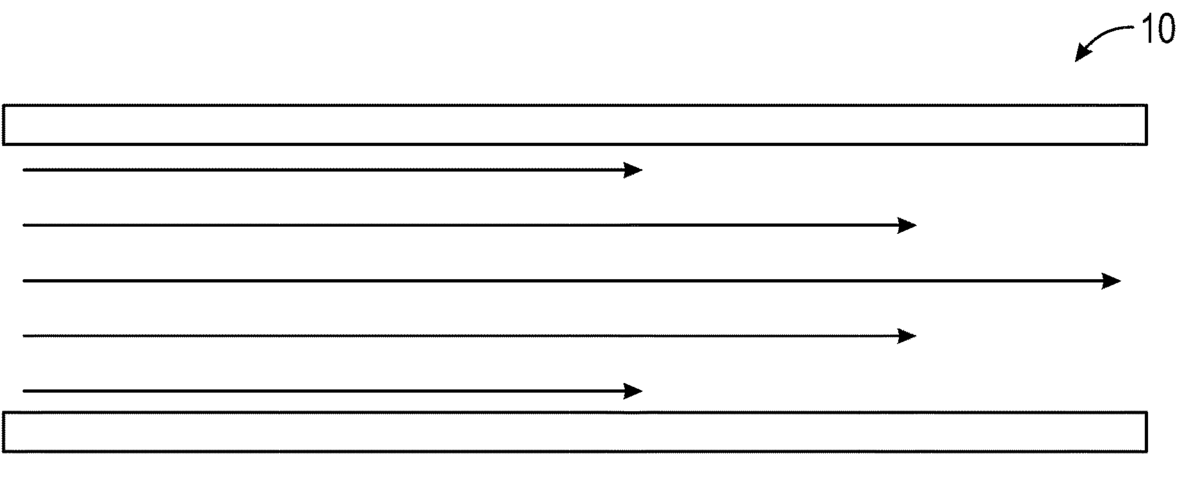
FIG. 1 shows a side view of a diagram showing a laminar flow of a prior art surgical aspirator without any constrictions in the tip.
Figure 2:
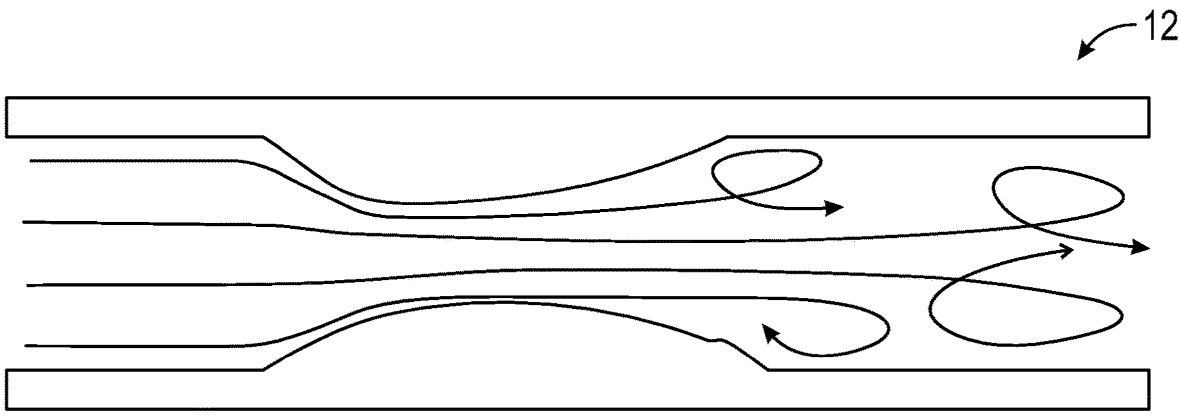
FIG. 2 shows a side view of a diagram showing a turbulent flow of a prior art surgical aspirator with a constricted tip.
Figure 3:
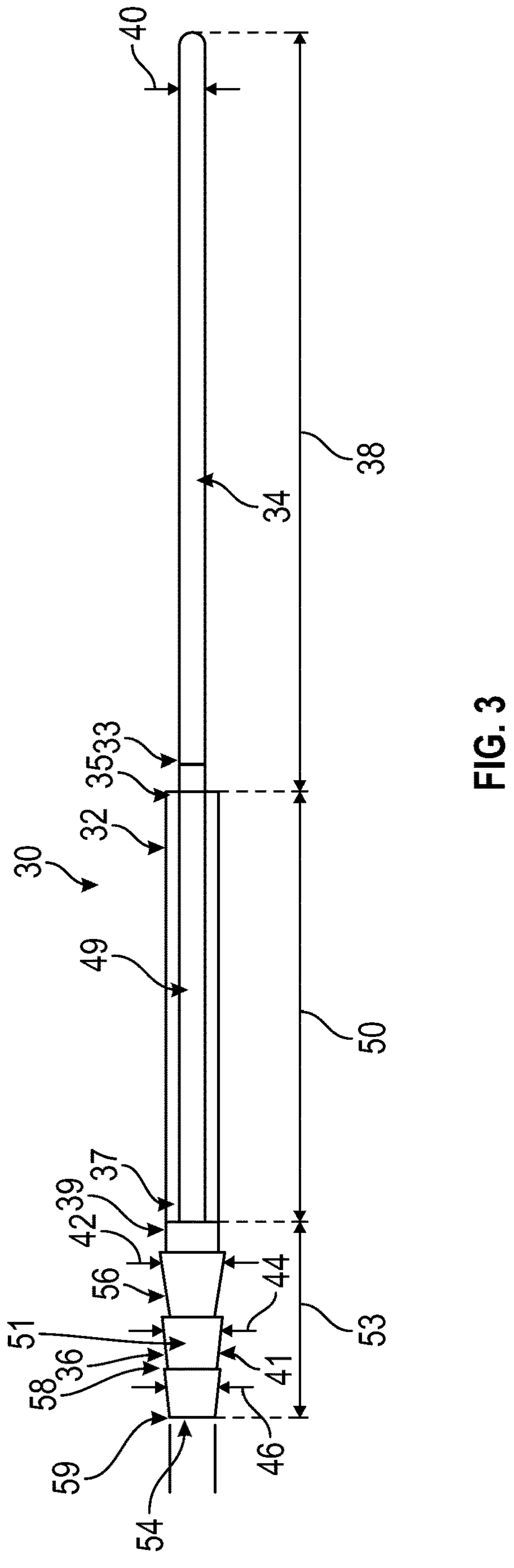
FIG. 3 shows a side plan view of the noise-reducing surgical aspirator of the present invention, including a tube, a handle, and a tip.

Referring now to FIG. 3, the surgical aspirator of the present invention is generally indicated by the numeral 30. The rear portion of the surgical aspirator 30 is tube 34, which can vary in length 38 depending on the application and is typically 96.4 millimeters. Likewise, the outer diameter 40 of tube 34 can vary by application and is typically 8.66 millimeters.

The tube 34 is directly connected to handle 32 so that the user can move and position the surgical aspirator 30. The handle 32 includes a first-end portion 35 and a second-end portion 37. Moreover, the handle 32 includes a handle length 50 that can range in length depending on the application and ergonomic considerations. The handle 32 is preferably 56 millimeters. In addition, there is a cylindrical insert 33 at the first end portion 35 of the handle 32 for connecting, in a fluid relationship, the second end portion of the handle 37 and tube 34, so that tube 34 is in fluid communication with the handle 32. Finally, the handle 32 includes an internal fluid conduit 49. The geometric adjustments in the present invention are concentrated in the surgical aspirator tip, which is generally indicated by the numeral 36, with the remainder of the surgical aspirator can be a standard 8 French tube.

There are a wide variety of materials that can be used for manufacturing the surgical aspirator 30 which are acceptable for FDA approval. The duration of implantation is not applicable in this application, and the duration of contact is less than 30 days. FDA testing requirements include modulus, yield strength, ultimate strength, creep, fatigue, and abrasive wear, all in consideration of the orientation of the device as well as dimension measurements and tolerance.

The preferred metals have high electrical and thermal conductivity and are malleable and ductile. In addition, a titanium alloy (Ti, 6Al, 4V, Fe) provides more flexibility, is forty percent lighter than stainless steel, and is biocompatible. Other suitable metals include stainless steel grade 304 with, preferably, seventeen to twenty-five percent chromium and stainless steel grade 316, which includes up to seven percent iron, chromium, and molybdenum for additional corrosion resistance (in acidic environments). This metal does include nickel.

There are a wide variety of plastics that can be used for manufacturing surgical aspirator 30. Typically, these are large molecule polymers that include, but are not limited to, PLLA, PMMA, PEEK and Silicone, PP, PET, PU, and ABS. In addition, PLA can be utilized, which is non-toxic and used for medical implants, and biodegradable by hydrolysis.

Also, PEG can be blended with acrylate resins via SLA as a viable polymer. In addition, PCL (polycaprolactone) can be utilized, which is slowly biodegradable by hydrolysis and printable with FDM. Moreover, BioMed SLA resins (proprietary) plus PP and PU resins can be utilized. In addition, polyamide (nylon PA-12)-compatible with SLS and FDM that is sterilizable, can be used.

In addition, inorganic ceramics, which have high strength, hardness, high melting temperature, and are chemically inert with low thermal and electrical conductivity, can be utilized for the surgical aspirator 30. However, ceramics are more brittle than other materials (oxide, nitride, carbide).

Moreover, both naturally derived materials (animal or non-animal) and composites, e.g., a mixture of two or more distinct materials, can be used for the surgical aspirator 30.

The surgical aspirator 30 could be made from any of these materials. Preferably, the most likely material would be stainless steel for a durable device or polypropylene (PP)/ABS (acrylonitrile butadiene styrene) for a disposable version.

There is a series of sloping conical portions, preferably three, extend to the surgical aspirator tip opening 54 as shown in FIG. 3. The first sloping conical portion 56 is typical for surgical aspirators and has an initial diameter 42, which is typically 9.40 millimeters for surgical aspirators 30. The second sloping conical portion 58 includes an initial diameter 44 that is typically 8.76 millimeters for surgical aspirators 30. Finally, the third sloping conical portion 59 has an initial diameter 46, which is typically 8.10 millimeters for surgical aspirators 30.

Figure 4:
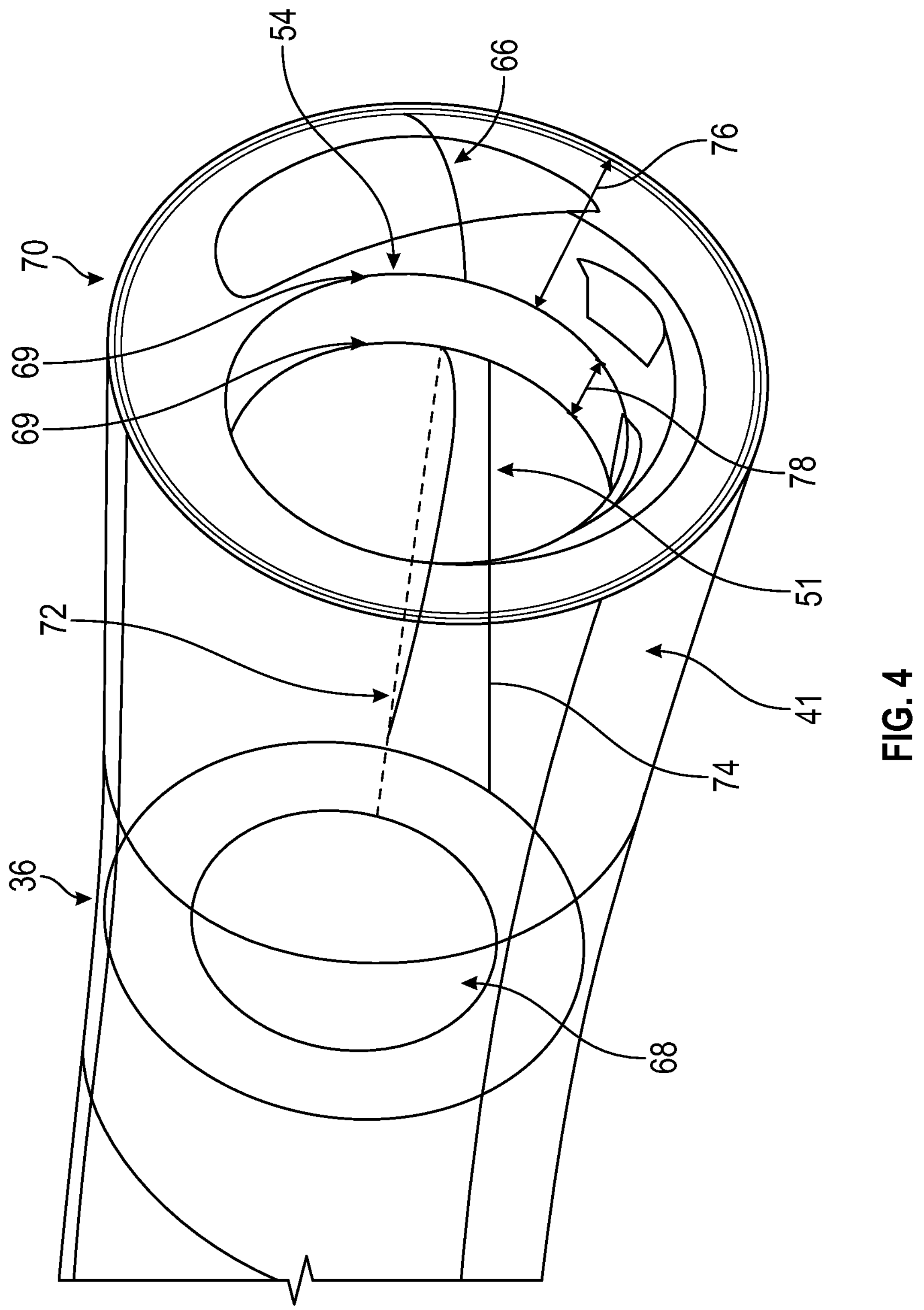
FIG. 4 shows a perspective sectional view of the surgical aspirator tip of the present invention.

Referring now to FIG. 4, the surgical aspirator tip 36 is shown in greater detail. There is a first inner recessed radius 68 that is approximately equivalent to the radius of a standard surgical aspirator, e.g., 8 French tube. 8 French tube is between 2.67 to 8.34 millimeters.

A "fillet" is defined as a rounded transition between adjacent faces of a three-dimensional object. There is a first fillet 72 that extends from the point of the first inner recessed radius 68 along a first fillet distance 74. This first fillet distance 74 preferably can extend in a range from the entire length of the surgical aspirator 30 down to one millimeter prior to the surgical aspirator tip opening outlet 54.

At the end of the first fillet 72, there is a second radius 69 that is in a range of between 1.2 times the first inner recessed radius 68 to two times the first inner recessed radius 68, which is referenced above as 8 French tube.

After the second radius 69, there is a second fillet 66 located between the second radius 69 and a third radius 70. The distance 78 between the first fillet 72 and a second fillet 66 is preferably in a range of zero to two millimeters. The second radius 69 can extend a third distance 78 between the first fillet 72 and a second fillet 66. The second radius 69 can range from a minimum of 1.2 times the aforementioned first inner recessed radius 69 to a maximum of two times the first inner recessed radius 68.

The third radius 70 can literally extend to a substantial value; having this third radius 70 be less than three times the first inner recessed radius 68 is the most reasonable from a commercially practical perspective, while the minimum should be at least 1.2 times the first inner recessed radius 68. The second fillet distance 76 should have a minimum of 0.4 millimeters but can extend for as long as practical. This third radius 70 is the outer diameter at the surgical diameter tip opening 54 and is preferably 5.8 millimeters. The length 53 of the surgical aspirator tip 36, as shown in FIG. 3, is preferably 25.48 millimeters. The associated radiuses of the first fillet 72 and the second filet 66 are as large as the geometry can allow under the previously described constraints.

The surgical aspirator tip 36 includes an internal fluid conduit 51, whereas the tube 34, internal fluid conduit 49 of the handle 32, and the internal fluid conduit 51 of the surgical aspirator tip 36 are all in fluid communication, as shown in FIG. 3. The surgical aspirator tip 36 includes a first end portion 39 that is attached to the second end portion 37 of the handle 32 and a second end portion 41 that includes the surgical aspirator tip opening 54.

The "length," which is the distance between the start and end of the curve of either the first fillet 72 or the second fillet 66, can be calculated by SOLIDWORKS® software. SOLIDWORKS® is a federally registered trademark of Dassault Systemes SolidWorks Corporation, having a place of business at 175 Wyman Street, Waltham, Massachusetts 02451. First, a radius is inputted into the SOLIDWORKS® software, which then checks if the radius is compatible with the geometry of the design. If it is compatible, then the SOLIDWORKS® software will insert the fillet so that the peak of the curve is equidistant between the two surfaces where the filleting is taking place. As for manufacturing, a 3D resin printer can be used with no specialized equipment to create the first fillet 72 or the second filet 66.

In order to adjust the size of the opening, the inner opening diameter, as well as the first fillet 72 and second fillet 66, may need to be adjusted, while the third outer radius 70 and the first inner recessed radius 68 stay the same.

As stated previously above, fillets round off edges, which is shown clearly in the second fillet 66. The curve of the edge is determined by a radius. The first fillet 72 makes it appear as though the taper between the first inner recessed radius 68 and the second radius 69 between the first fillet 72 and the second fillet 66 is linear. However, the taper is not linear, so fixed geometric angles cannot be used to define the taper.

Figure 5:
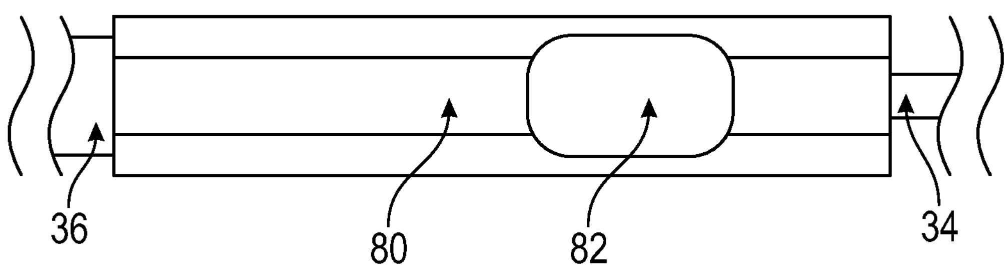
FIG. 5 shows a side view of a handle for the surgical aspirator tip of the present invention with a hexagonal grip and a thumb indent.
Figure 6:
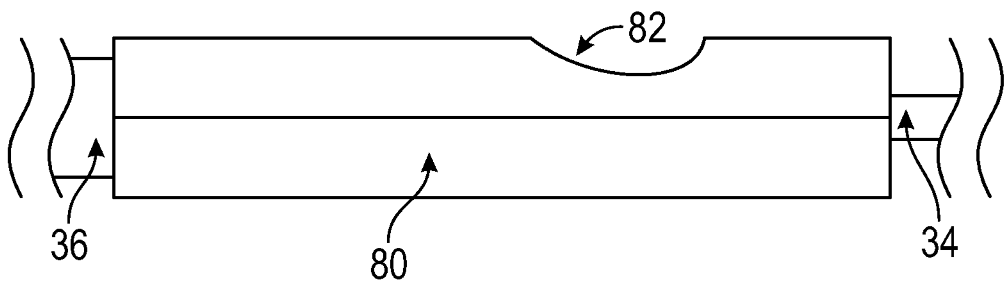
FIG. 6 shows a side view of a handle for the surgical aspirator tip of the present invention with a hexagonal grip and a thumb indent, as shown in FIG. 5, which is rotated ninety degrees clockwise.
Figure 7:
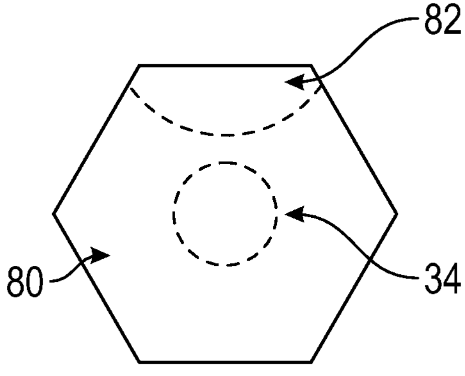
FIG. 7 shows a rear view of the hexagonal handle for the surgical aspirator tip of the present invention shown in FIGS. 5 and 6

There are a number of possible embodiments for the handle 32. Referring now to FIGS. 5, 6, and 7, a hexagonal handle is generally indicated by numeral 80. In addition, there is a thumb indentation indicated by numeral 82. The same tube 34 and surgical aspirator tip 36 are also shown through two side views rotated ninety degrees and one back view of the hexagonal handle 80, as shown in FIGS. 5, 6, and 7, respectively.

Figure 8:
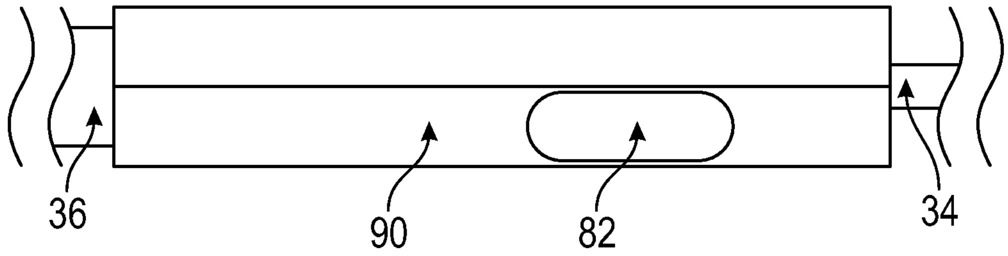
FIG. 8 shows a side view of a handle for the surgical aspirator tip of the present invention with a triangular grip and a thumb indent.
Figure 9:
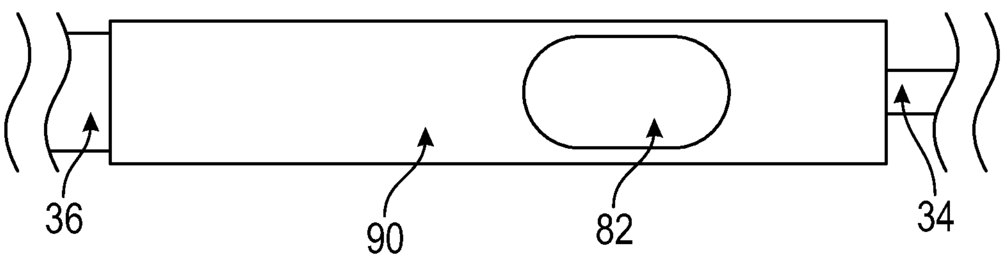
FIG. 9 shows a side view of a handle for the surgical aspirator tip of the present invention with a triangular grip and a thumb indent, shown in FIG. 8, that is rotated one hundred and twenty degrees clockwise.
Figure 10:
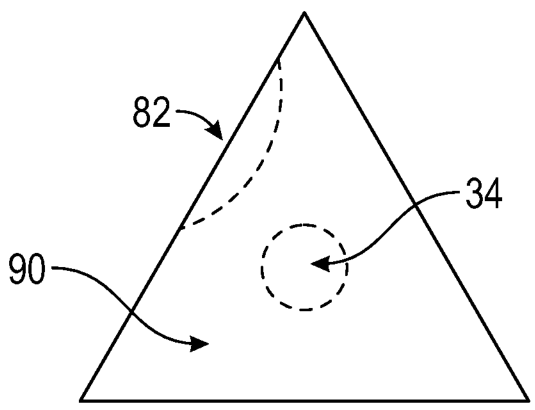
FIG. 10 shows a rear view of the triangular handle for the surgical aspirator tip of the present invention shown in FIGS. 8 and 9

Referring now to FIGS. 8, 9, and 10, a triangular handle is generally indicated by numeral 90. The same thumb indentation indicated by numeral 82 is present that was previously shown in FIGS. 5, 6, and 7, above. The same tube 34 and surgical aspirator tip 36 are also shown through two side views rotated ninety degrees and one back view of the triangular handle 90, shown in FIGS. 8, 9, and 10, respectively.

Figure 11:
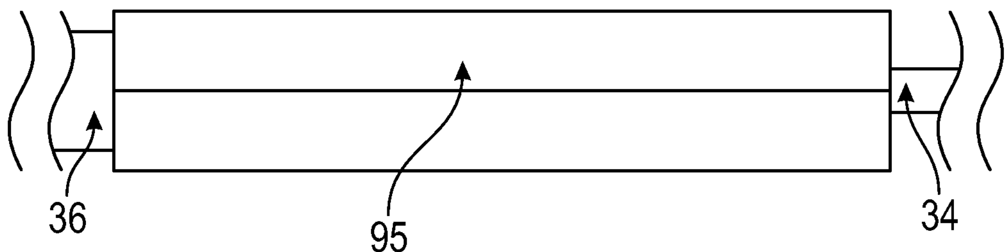
FIG. 11 shows a side view of a handle for the surgical aspirator tip of the present invention with a triangular grip and no thumb indent.
Figure 12:
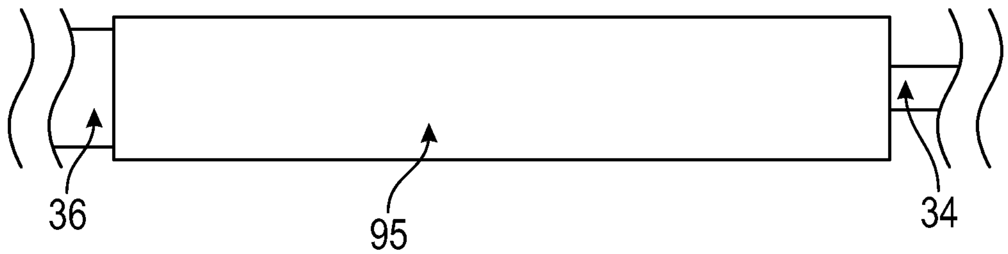
FIG. 12 shows a side view of a handle for the surgical aspirator tip of the present invention with a triangular grip and no thumb indent, shown in FIG. 11, which is rotated one hundred and twenty degrees clockwise.
Figure 13:
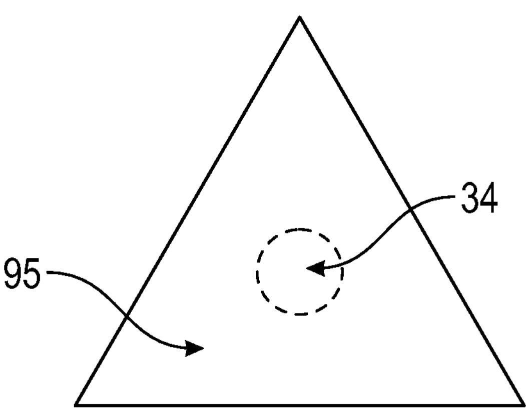
FIG. 13 shows a rear view of the triangular handle for the surgical aspirator tip of the present invention shown in FIGS. 11 and 12, which does not have a thumb indent.

Referring now to FIGS. 11, 12, and 13, a triangular handle is generally indicated by numeral 95. However, there is no thumb indentation in this embodiment. The same tube 34 and tip 36 are also shown through two side views rotated ninety degrees and one back view of the triangular handle 95, shown in FIGS. 11, 12, and 13, respectively.

Therefore, the surgical aspirator of the present invention can provide a novel device that complies with ISO 10079, ISO 10993, and ISO 3744. ISO 10079 reduces the harmful effects of noise by reducing sound power and sound energy, improving safety and performance, and providing biocompatibility. In addition to significantly reducing the noise of turbulent flow, the present invention is also low-cost, sterilizable, user-friendly, and serves the surgical aspirator's purpose of suctioning.

From the foregoing, it can be seen that the present invention accomplishes at least all of the stated objectives.

LIST OF REFERENCE CHARACTERS

The following table of reference characters and descriptors is not exhaustive or limiting and includes reasonable equivalents. If possible, elements identified by a reference character below and/or those elements which are near ubiquitous within the art can replace or supplement any element identified by another reference character.

TABLE 1

| List of Reference Characters |
|---|
| 10 Laminar Flow |
| 12 Turbulent Flow |
| 30 Surgical Aspirator |
| 32 Handle |
| 33 Cylindrical Insert |
| 34 Tube |
| 35 First End Portion of Handle |
| 36 Surgical Aspirator Tip |
| 37 Second End Portion of Handle |
| 38 Tube Length |
| 39 First End Portion of Surgical Aspirator Tip |
| 40 Outer Diameter of the Tube |
| 41 Second End Portion of Surgical Aspirator Tip |
| 42 Initial Diameter of First Sloping Conical Portion |
| 44 Initial Diameter of Second Sloping Conical Portion |
| 46 Initial Diameter of Third Sloping Conical Portion |
| 48 Outer Diameter of the Tip Opening |
| 49 Internal Fluid Conduit of Handle |
| 50 Handle Length |
| 51 Internal Fluid Conduit of Surgical Aspirator Tip |
| 53 Length of the Tip |
| 54 Surgical Aspirator Tip Opening |
| 56 First Sloping Conical Portion |
| 58 Second Sloping Conical Portion |
| 59 Third Sloping Conical Portion |
| 64 Diameter Distance Between Inner Recessed Diameter and Inner Opening Diameter |

TABLE 1-continued

| List of Reference Characters |
|---|
| 66 Second Fillet |
| 68 First Inner Recessed Radius |
| 69 Second Radius Between the First Fillet and the Second Fillet |
| 70 Third Outer Radius |
| 72 First Fillet |
| 74 First Distance of First Fillet |
| 76 Second Distance of Second Fillet |
| 78 Third Distance Between the First Fillet and the Second Fillet |
| 80 Hexagonal Handle |
| 82 Thumb Indentation |
| 90 Triangular Handle with Thumb Indentation |
| 95 Triangular Handle without Thumb Indentation |

GLOSSARY

Unless defined otherwise, all technical and scientific terms used above have the same meaning as commonly understood by one of ordinary skill in the art to which embodiments of the present invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein, refers to slight variations in numerical quantities with respect to any quantifiable variable. Inadvertent error can occur, for example, through the use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes a structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

What is claimed is:

1. A noise-reducing surgical aspirator comprising, a tube;

a handle, having a first end portion, a second end portion, and a first internal fluid conduit, where the first end portion of the handle is attached to the tube in fluid communication; and a surgical aspirator tip having a second internal fluid conduit that is in fluid communication with the first internal fluid conduit of the handle and having a first end portion attached to the second end portion of the handle and having a second end portion that includes an opening, wherein the second internal fluid conduit of the surgical aspirator tip includes a first inner recessed radius and a second radius with a first fillet located between the first inner recessed radius and the second radius and includes a third outer radius of the opening and a second fillet located between the second radius and the third outer radius, wherein the first fillet has a length that is in a range between a length of the noise-reducing surgical aspirator and is greater than one millimeter and the second fillet has a length that is greater than four millimeters, and the first inner recessed radius has a radius that is comparable to a radius of the tube and the second radius has a radius that is a range of two times the first inner recessed radius to 1.2 times the first inner recessed radius, the second radius extends a length that is in a range from zero millimeters to two millimeters, and the third outer radius has a radius that is a range of three times the first inner recessed radius to 1.2 times the second radius.

2. The noise-reducing surgical aspirator, according to claim 1, wherein the handle includes a thumb indentation.

3. The noise-reducing surgical aspirator, according to claim 1, wherein the handle is hexagonally shaped.

4. The noise-reducing surgical aspirator, according to claim 3, wherein the hexagonally shaped handle includes a thumb indentation.

5. The noise-reducing surgical aspirator, according to claim 1, wherein the handle is triangularly shaped.

6. The noise-reducing surgical aspirator, according to claim 5, wherein the triangularly shaped handle includes a thumb indentation.

7. A method for utilizing a noise-reducing surgical aspirator, comprising:

attaching a tube to a handle, having a first end portion, a second end portion, and a first internal fluid conduit, where the first end portion of the handle is in fluid communication with the tube; and attaching a surgical aspirator tip, having a second internal fluid conduit that is in fluid communication with the first internal fluid conduit of the handle and having a first end portion attached to the second end portion of the handle, and having a second end portion that includes an opening, wherein the second internal fluid conduit of the surgical aspirator tip includes a first inner recessed radius and a second radius with a first fillet located between the first inner recessed radius and the second radius and includes a third outer radius of the opening and a second fillet located between the second radius and the third outer radius; wherein the first fillet has a length that is in a range between a length of the noise-reducing surgical aspirator and is greater than one millimeter and the second fillet has a length that is greater than four millimeters, and the first inner recessed radius has a radius that is comparable to a radius of the tube and the second radius has a radius that is a range of two times the first inner recessed radius to 1.2 times the first inner recessed radius, the second radius extends a length that is in a range from zero millimeters to two millimeters, and the third outer radius has a radius that is a range of three times the first inner recessed radius to 1.2 times the second radius.

* * * * *